United States Patent [19]

Klein

[11] Patent Number: 4,809,678

[45] Date of Patent: Mar. 7, 1989

[54] ENDOSCOPE FOR PREVENTING PATIENT CONTAMINATION

[76] Inventor: Richard S. Klein, 46 Annandale Dr., Chappaqua, N.Y. 10514

[21] Appl. No.: 85,500

[22] Filed: Aug. 14, 1987

[51] Int. Cl.$^4$ ............................................. A61B 1/00
[52] U.S. Cl. ...................................................... 128/4
[58] Field of Search .................... 128/3, 4, 5, 6, 7, 23, 128/768

[56] References Cited

U.S. PATENT DOCUMENTS

| | | | |
|---|---|---|---|
| 3,794,091 | 2/1974 | Ersek et al. ...................... | 128/23 X |
| 3,809,072 | 5/1974 | Ersek et al. ...................... | 128/23 |
| 4,168,699 | 9/1979 | Hauser ............................. | 128/768 |
| 4,646,722 | 3/1987 | Silverstein et al. ................ | 128/4 |
| 4,741,326 | 5/1988 | Sidall et al. ..................... | 128/4 |

*Primary Examiner*—William H. Grieb
*Attorney, Agent, or Firm*—Wolder, Gross & Yavner

[57] ABSTRACT

An endoscope construction wherein a basic endoscope instrument is covered substantially, over the part which normally contacts the patient, with a condom-like sheath, elastsicized at one or both of its ends in order to prevent contamination from one patient to the other.

2 Claims, 1 Drawing Sheet

ENDOSCOPE FOR PREVENTING PATIENT CONTAMINATION

BACKGROUND OF THE INVENTION

This invention relates primarily to endoscope constructions and more particularly to such constructions useful for preventing contamination from one patient to the other, upon which the instrument is used.

Endoscopes are medical instruments for introduction to body openings of patients. In basic construction, they are cylindrical and elongated with flexible tubing connecting the distal and proximal ends. Such instruments vary in length from one foot to five feet and usually vary in diameter between ¼ and ¾ of an inch. In just about all cases, the instrument is intended for repeated use and is costly enough so that physicians and most hospitals maintain in stock only one or two such instruments; but nevertheless, such instruments are used three or four times, or more, during an average day. Most manufacturers of such instruments recommend that the instrument be "disinfected" between uses. In recent months, sterlization of such instruments has been recommended for endoscopes, mostly because of the onset of the AIDS epidemic. Sterlization usually can take either of two forms; namely, autoclaving or gas sterlization. Because of the usual materials used for constructing endoscope instruments, auto-claving would probably melt, or at least somewhat distort the materials of the endoscope. Therefore, gas sterilization is usually the procedure taken since the recent concern relating to AIDS. Unfortunately, gas sterilization involves a twenty-four hour process, which provides the private practice physician or hospital only the choice of purchasing additional instruments, thereby increasing the already high cost of medical treatment, or being unprepared for certain patients who require an endoscope procedure.

Of course, disinfection is unsatisfactory, in view of the AIDS epidemic, since it does not affect the AIDS virus.

It should also be understood that endoscope instruments commonly involve means for inserting air, suction and biopsy forceps, as well as viewing fibers to be inserted through and beyond the distal end of the instrument.

The endoscope instrument has remained relatively constant in construction for many years. Various modifications to the structure of the instrument have been suggested, but for purposes different than those accomplished by the present invention. For instance, Hauser, in U.S. Pat. No. 4,168,699, issued Sept. 25, 1979, suggested a particular catheter construction, whose main purpose and accomplishment was to prevent contamination to a patient sample being withdrawn from a body cavity. The construction suggested by Hauser could not, and was not intended to, solve the problem addressed by the present invention, as it relates to preventing contamination from one patient to the other upon which the instrument is used.

Accordingly, a primary object of the present invention is to provide an endoscope construction which prevents contamination from one patient to the other, because of body fluid interchange between the first patient and the instrument, and then between the instrument and a second patient.

A further and more particular object of the present invention is to provide disposable and replaceable construction means to protect against such contamination.

BRIEF SUMMARY OF THE INVENTION

These and other objects of the present invention are provided in an endoscope construction for substantially protecting the basic endoscope instrument from viral and bacterial contamination from one patient to another. The endoscope instrument, near its proximal end, is attached to the first end of an elongated covering sheath, and its distal end is attached to the second sheath end. The sheath is constructed of a material which is flexible, watertight, disposable and replaceable. For instance, a rubber-like and condom-like material is used which could be removed and replaced in conjunction with disinfecting of the basic instrument, in order to prevent cross-contamination, as described. Furthermore, the construction enables the use of the same basic instrument on more than one patient in a given period, for instance, less than twenty-four hours, as is currently done, but now with virtually no fear of infesting a later patient with AIDS, because of the use of the instrument earlier on a patient contaminated with the AIDS virus. The first attachment described in the foregoing is by elasticized fitting of the sheath at its first end and either elasticized fitting at the second end or for covering the distal end of the basic end instrument with a window portion enabling the passage of air, suction, biopsy forceps and/or viewing through fibers placed end-to-end in the instrument. More particularly, the window portion could be provided with flexible slit flaps, or, in the alternative, simply a clear window-portion, with no slits could be used. Of course, a combination of the two would be more suitable for multiple usages, as described, but somewhat less protective. Also, alternatively, the sheath could be elasticized at its second end with the distal tip of the basic endoscope instrument removable and replaceable from one patient to the other. Considering all of the above alternatives, perhaps the most protective would be the elasticized fitting at the second end of the sheath proximate the distal end of the basic instrument, which protects more than 99% of the instrument from contamination, and yet disinfecting, using suitable solutions, combined with such a sheath, would most suitably accomplish the purposes of the present invention, in the least expensive and most convenient manner.

The above brief description as well as further objects, features and advantages of the present invention, will be more fully appreciated by reference to the following detailed description of the preferred, but nonetheless illustrative, embodiment, when taken in conjunction with the accompanying drawings, wherein:

BRIEF DESCRIPTION OF THE DRAWINGS

FIG. 2b is a view of the invention, similar to that shown in FIGS. 2 and 2a, with flexible slit flaps at the end of the sheath for a protrusion of forceps, the passage of air, or the like.

FIG. 1 shows an endoscope construction according to the present invention, which includes a conventional, flexible, basic endoscope, generally designated 10 commonly used in the medical field. The conventional, basic endoscope has an operating end 12 which permits, by manipulation of the physician, a variety of operations to be performed. The conventional endoscope is also provided with a distal end 14, the operating or proximate end 12 and the distal end 14 being connected by an elongated flexible portion 16. Usually the operating end is provided with an eye piece assembly 18, one or more control knobs 20, an inlet opening 19 through which an instrument such as forceps is inserted, an air and/or water feed control device 22, a suction control (not shown) and a light inlet means 24. With respect to the operating end 12, many of the above listed facilities are connected and/or connectible. For instance, an illumination light source (not shown) is arranged to connect with light inlet means 24, which in turn connects through the endoscope, to the distal end 14 in order to illuminate a body cavity or opening to the patient for examination or treatment.

Normally, a bundle or bundles of fiber optic devices, known as optical fibers extend through the flexible portion 16 in order to image and guide light from one end of the instrument to the other. Furthermore, various tubes and channels are provided in the flexible portion 16 to contain the air, water, suction and/or treatment instrument for control at the proximate end and operation at the distal end of the endoscope.

According to the present invention, a flexible, rubber or condom-like material 26 is provided to encircle the flexible portion of the endoscope, with elasticized ends 28, 30 (FIG. 2a) preventing contamination of the instrument over a substantial portion of its length. The elasticized end 30 at the distal end of the endoscope is arranged to snugly fit at approximately the ultimate end of the instrument, so that only the small proportion of the endoscope represented by its end face can possibly be contaminated and thereby be a conduit of contamination from one patient to the other. Disinfection, as per the usual procedure with an endoscope, would be used to clean between uses. However, disinfection is not sufficient to destroy the AIDS virus, and others.

Figure 1:
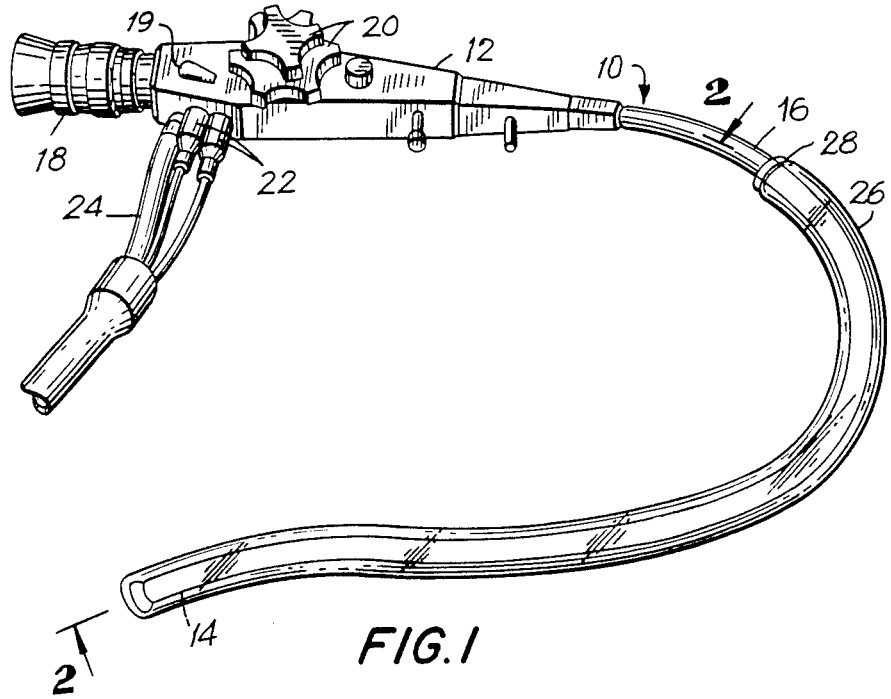
FIG. 1 is a plan view of an endoscope contructed according to the present invention.
Figure 2:
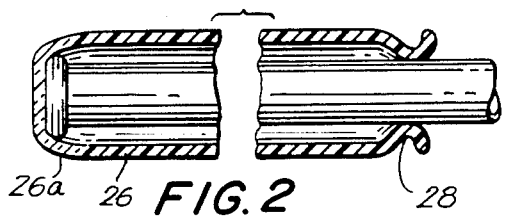
FIG. 2 is a sectional view of the construction of FIG. 1, showing particularly the sheath portion of the endoscope of FIG. 1 and the construction involving a clear window portion for the sheath.

More specifically, in all embodiments in this invention, the proximate end of sheath 26 is elasticized to prevent contamination of the basic instrument 10 by its use. FIG. 2 shows a sectional view of the invention construction whereby the distal end portion 26a of sheath 26 is transparent and translucent for purposes of use of the instrument, as described. Thus, in this form, the present invention provides the protection desired, but with the capability only of certain uses of the instrument, such as viewing body cavities and the like, but not forceps insertion.

Figure 2A:
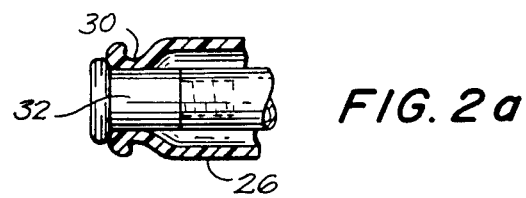
FIG. 2a is a view, similar to that shown in FIG. 2, but with an elasticized sheath end and a removable end portion for the basic endoscope instrument.

Thus, the alternative embodiment of FIG. 2a, wherein distal end 30 of sheath 26 is elasticized, enables more varied use of the instrument. In particular, the embodiment of FIG. 2a has a removable, basic instrument end 32, so that between consecutive uses, the end 32 could be removed and replaced along with the sheath 26. End 32 could then be gas-sterilized, the sheath 26 thrown away, a new sheath 26 provided, then the economy of multiple, replaceable ends 32, as distinguished from multiple instruments, is readily apparent.

Figure 2B:
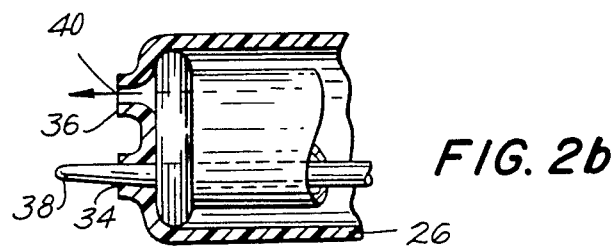

A further alternative embodiment is shown in FIG. 2b whereby sheath 26 is provided with slit-flaps 34, 36 to offer the protection addressed previously herein, but with the capability for the protrusion of forceps 38 and the insertion of air 40 to body cavities and openings being a capability of the construction.

As may be seen from the foregoing, construction according to the present invention provides protection for patients, with whom the basic endoscope instrument is used. Such construction, and its scope of protection, is to be limited only by the following claims, in terms of the scope of protection for the invention.

I claim:

1. An endoscope construction for substantially protecting the basic endoscope from viral and bacterial contamination from one patient to another comprising a basic endoscope instrument having a distal end face and a distal end, over which is placed, in conforming relationship to the distal end of the basic instrument, a flexible, watertight, disposable and replaceable rubber-like material in elongated sheath form, including a proximal, elasticized fitting proximate the proximal end of the basic endoscope instrument and means at the distal end of the basic endoscope instrument for substantially protecting the part of the basic endoscope instrument which comes into contact with the patient, said basic endoscope instrument comprising a removable distal end portion, which includes said end face, and said means including an elasticized fitting for substantially covering the distal end of said basic endoscope instrument, except for end face.

2. An endoscope construction for substantially protecting the basic endoscope from viral and bacterial contamination from one patient to another comprising a basic endoscope instrument having a distal end face and a distal end, over which is placed, in conforming relationship to the distal end of the basic instrument, a flexible, watertight, disposable and replaceable rubber-like material in elongated sheath form, including a proximal, elasticized fitting proximate the proximal end of the basic endoscope instrument and means at the distal end of the basic endoscope instrument for substantially protecting the part of basic endoscope instrument which comes into contact with the patient, said means including a window portion defining multiple end slit flaps.

* * * * *